US00PP24693P3

(12) United States Plant Patent
Egger

(10) Patent No.: US PP24,693 P3
(45) Date of Patent: Jul. 22, 2014

(54) ***SEDUM* PLANT NAMED 'THUNDERHEAD'**

(50) Latin Name: ***Sedum* hybrid (syn. *Hylotelephium*)**
Varietal Denomination: Thunderhead

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 120 days.

(21) Appl. No.: 13/573,978

(22) Filed: Oct. 16, 2012

(65) Prior Publication Data

US 2014/0109279 P1 Apr. 17, 2014

(51) Int. Cl.
*A01H 5/00* (2006.01)

(52) U.S. Cl.
USPC ..... Plt./479

(58) Field of Classification Search
USPC ..... Plt./479
See application file for complete search history.

*Primary Examiner* — Susan McCormick Ewoldt

(74) *Attorney, Agent, or Firm* — Klarquist Sparkman, LLP

(57) ABSTRACT

A new and distinct hybrid of *Sedum* plant substantially as shown and described, characterized by medium deep red purple flowers in very large inflorescences, dusky, dark leaves, strong, upright stems, and a medium, clumping habit.

1 Drawing Sheet

Botanical denomination: *Sedum* hybrid (syn. *Hylotelephium*).

Variety designation: 'Thunderhead'.

Parentage: *Sedum telephium* 2-5×*Sedum spectabile* 'Neon'.

BACKGROUND OF THE INVENTION

The present invention relates to a new and distinct cultivar of *Sedum* and given the cultivar name of 'Thunderhead'. *Sedum* is in the family Crassulaceae. *Sedum* 'Thunderhead' originated from a planned breeding program to produce hybrids with dark leaves, short stems and large inflorescences. *Sedum* 'Thunderhead' originated from a cross between an unnamed, proprietary, an unpatented *Sedum telephium* 2-5 as the seed parent and *Sedum spectabile* 'Neon', unpatented, as the pollen parent.

Compared to the seed parent *Sedum telephium* 2-5, the new cultivar is has much larger inflorescences with better flower color, and larger, lighter colored leaves.

Compared to the pollen parent, *Sedum spectabile* 'Neon', the new cultivar, has leaves that are a dusky gray green color rather than yellow green.

Compared to *Sedum* 'Class Act' (U.S. Plant Pat. No. 20,125), the new variety is taller with leaves that dark rather than green with dark margins. The flowers of the new variety are smaller in larger, denser, and flatter inflorescences. The flowers of the new variety are more purple in color.

Compared to *Sedum* 'Beach Party', (U.S. Plant Pat. No. 22,810), the new variety is larger in habit, and has darker leaves and flowers.

This new and unique *Sedum* is distinguished by:

1. medium deep red purple flowers in very large inflorescences,
2. dusky, dark leaves,
3. strong, upright stems, and
4. a medium, clumping habit.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a two-year-old *Sedum* 'Thunderhead' growing in the garden in August in Canby, Oreg.

FIG. 2 shows a two-year-old *Sedum* 'Thunderhead' in a two gallon container in early September in full bloom in Canby, Oreg.

DETAILED PLANT DESCRIPTION

The following is a detailed description of the new *Sedum* hybrid based on observations of three-year-old specimens grown in a garden in full sun under typical outdoor conditions in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The *Royal Horticultural Society Colour Chart*, 5$^{th}$ edition.

Plant:

*Type.*—Herbaceous perennial.

*Hardiness.*—USDA Zone 4 to 9.

*Size.*—50 cm tall from the ground to the top of the inflorescence and 54 cm wide.

*Habit.*—Erect, clumping.

*Vigor.*—Excellent.

Stem:

*Number.*—About 24.

*Size.*—31 cm long and 11 mm wide.

*Internode length.*—3 to 20 mm long.

*Color.*—Greyed Purple 187A.

*Texture.*—Succulent.

*Surface.*—Glaucous.

Leaf:

*Type.*—Simple.

*Arrangement.*—Variable.

*Shape.*—Ovate to elliptic.

*Apex.*—Acute.

*Base.*—Clasping.

*Venation.*—Pinnate.

*Margins.*—Serrate.

*Blade size.*—Grows to 5.5 cm long and 3.6 cm wide.

*Surface.*—Glaucous.

*Texture.*—Thick, spongy, succulent.

*Petiole.*—Leaves sessile.

*Leaf color.*—Topside closest to Brown 200A including vein; bottom side Green 147B tinted Greyed Purple 187A including vein.

Inflorescence:

*Type.*—Terminal, corymbose, umbel-like.

Number of flowers.—Over 1000 per stem (increases with age).

*Pedicels.*—3 mm to 6 mm long, 1 mm wide, glabrous, Brown N200B.

*Peduncle.*—8 cm tall and 4 mm to 7 mm wide, Greyed Purple 187B, succulent, glaucous.

*Size.*—Grows to 18 cm tall and 21 cm wide.

*Bloom period.*—August through September in Canby, Oreg.

Flower bud:

*Size.*—2.5 mm wide, 5 mm deep.

*Description.*—Ovoid.

*Color.*—Greyed Purple 186D.

Flower:

*Type.*—Complete, actinomorphic.

*Shape.*—Stellate.

*Size.*—6 mm deep and 10 mm wide.

*Color.*—Red Purple 72A.

*Corolla description.*—10 mm wide and 4 mm deep, 5 petals, each lanceolate, 6 mm long and 2 mm wide, margins entire, tip acuminate, glabrous on both sides, top and bottom side Red Purple 72A on top ⅔ blending to Red Purple 70C on bottom ⅓.

*Calyx description.*—3 mm deep and 4 mm wide, stellate, 5 lobes, divided to the base, margins entire, tip acute, glabrous, Brown N200B on both sides.

*Stamen description.*—10 in number, 10.5 mm long, filaments 10 mm long, Red Purple 70B, anthers Greyed Purple 187A, pollen Yellow 4D, sterile.

*Pistil description.*—5 separate prominent carpels, each 4 mm deep and 1.5 mm wide, Red Purple 72A, style 2 mm long, style and stigma Purple 71A.

*Fragrance.*—None.

*Lastingness.*—Each stem lasts up to a month.

Fruit:

*Type.*—Ventrally dehiscent follicle, erect, attenuate.

*Fertility.*—None.

*Color.*—Greyed Purple 187A at top and gray tan at bottom, Grey 200B.

Seed: No seed produced.

Disease and pest resistance or tolerance: Pest and disease resistance are typical for this type of *Sedum*. No known resistances.

I claim:

1. A new and distinct hybrid of *Sedum* plant as herein illustrated and described.

* * * * *

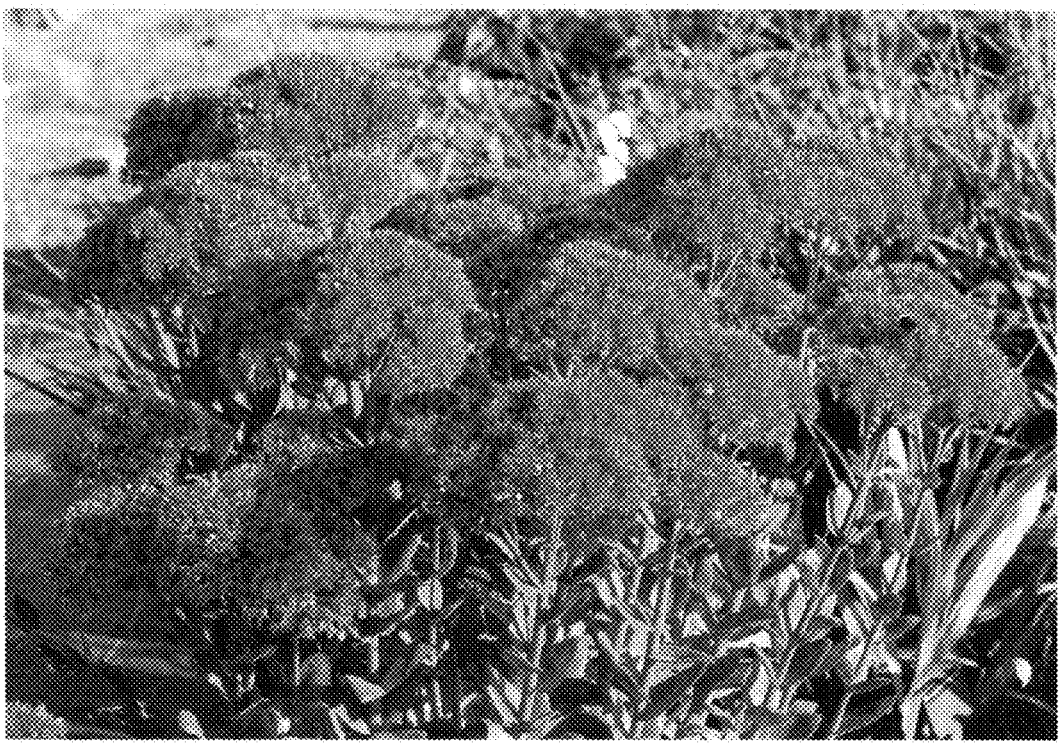

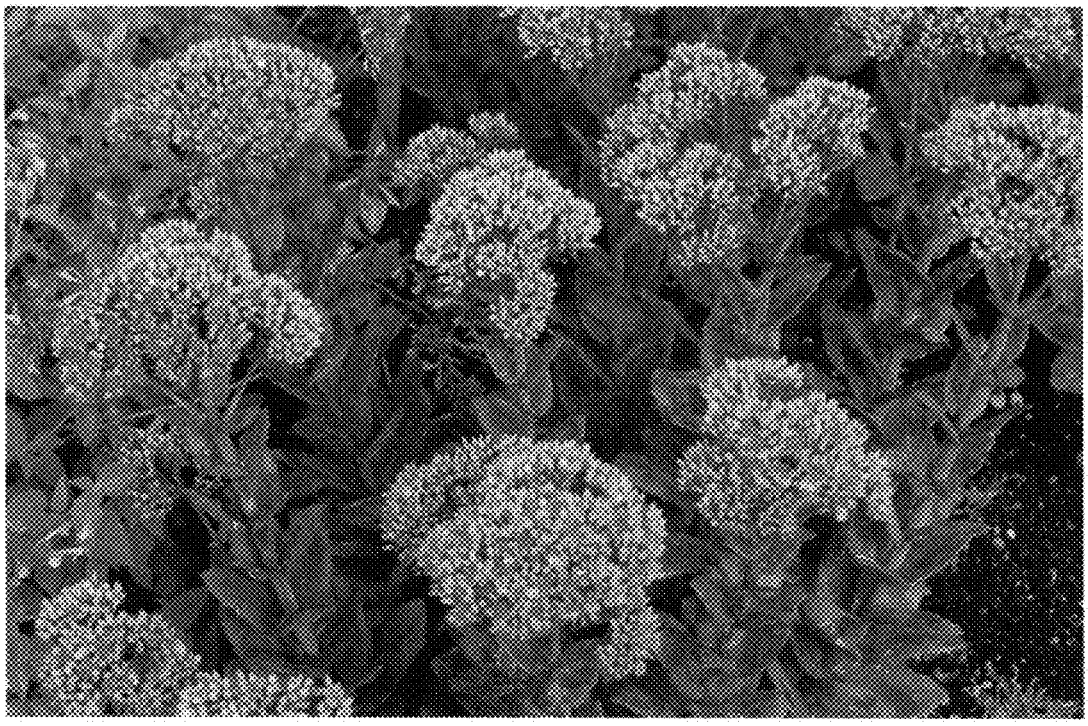
FIG. 1 above, FIG. 2 below